United States Patent
Reddy et al.

(10) Patent No.: US 11,718,633 B2
(45) Date of Patent: Aug. 8, 2023

(54) INDOLE COMPOUNDS, PROCESS FOR THE PREPARATION AND USE THEREOF

(71) Applicant: COUNCIL OF SCIENTIFIC AND INDUSTRIAL RESEARCH, New Delhi (IN)

(72) Inventors: Dumbala Srinivasa Reddy, Pune (IN); Sidharth Chopra, Lucknow (IN); Rahul Dilip Shingare, Pune (IN); Sreenivasa Rao Ramana, Pune (IN); Arunava Dasgupta, Lucknow (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 74 days.

(21) Appl. No.: 17/056,081

(22) PCT Filed: May 15, 2019

(86) PCT No.: PCT/IN2019/050391
§ 371 (c)(1),
(2) Date: Nov. 17, 2020

(87) PCT Pub. No.: WO2019/220461
PCT Pub. Date: Nov. 21, 2019

(65) Prior Publication Data
US 2021/0238204 A1 Aug. 5, 2021

(30) Foreign Application Priority Data
May 17, 2018 (IN) .............................. 201811018423

(51) Int. Cl.
| | |
|---|---|
| *C07D 401/12* | (2006.01) |
| *C07F 7/08* | (2006.01) |
| *A61P 31/06* | (2006.01) |
| *C07D 209/42* | (2006.01) |

(52) U.S. Cl.
CPC ............ *C07F 7/0816* (2013.01); *A61P 31/06* (2018.01); *C07D 209/42* (2013.01); *C07D 401/12* (2013.01); *C07F 7/083* (2013.01)

(58) Field of Classification Search
CPC ................................................. C07D 401/12
See application file for complete search history.

(56) References Cited

FOREIGN PATENT DOCUMENTS

EP        2892880 B1        11/2017

OTHER PUBLICATIONS

Menon, et al. Journal of the Chemical Society (1931) 773-7 (abstract) Accession No. 1931:30095; retrieved from STN.*
Brown, et al. Journal of Organic Chemistry (1956), 21, 261-2.*
Laboratoires Francais de Chmiotherapie. FR 71 (abstract), Feb. 27, 1961; Accession No. 1963:8333; retrieved from STN.*
Szmuszkovicz, J. Journal of Organic Chemistry (1964), 29 (1), 178-84 (abstract) Accession No. 1964:23245; retrieved from STN.*
Allais, et al. FR 1363855 (abstract) Feb. 4, 1960, Accession No. 1964:484151, retrieved from STN.*
Pigulla, et al. Archiv der Pharmazie (Weinheim, Germany) (1979) 312(1), 12-18 (abstract), Accession No. 1979:151917, retrieved from STN.*
Yoshino, et al. WO 2001074774 (abstract) entered in STN on Oct. 12, 2001, Accession No. 2001:747751, retrieved from STN.*
Ahmed et al., Synthesis of New Functionalized Indoles Based on Ethyl Indol-2-carboxylate, Molecules 2016, 1-12, 21/333, www.mdpi.com/journal/molecules.
International Search Report and Written Opinion for Application No. PCT/IN2019/050391, filed May 15, 2019, dated Sep. 13, 2019.
Jozef Stec et al., Indole-2-carboxamide-based MmpL3 inhibitors show exceptional antitubercular activity in an animal model of tuberculosis infection, Jun. 8, 2016, Journal of Medicinal Chemistry, 6232-6247, 59(13), https://doi.org/10.1021/acs.jmedchem.6b00415.

* cited by examiner

*Primary Examiner* — Shawquia Jackson
(74) *Attorney, Agent, or Firm* — Workman Nydegger

(57) ABSTRACT

The present invention relates to an indole compound of Formula (I) or pharmaceutically acceptable salt thereof, and process for the preparation thereof. The present invention also relates to a pharmaceutical composition of indole compound of Formula (I) or pharmaceutically acceptable salt thereof for treating mycobacterial infection or antimalarial infection or antifungal infection in a subject in need thereof.

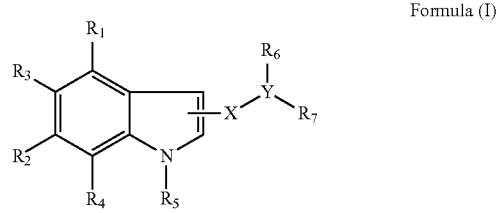

Formula (I)

7 Claims, No Drawings

INDOLE COMPOUNDS, PROCESS FOR THE PREPARATION AND USE THEREOF

FIELD OF THE INVENTION

The present invention relates to an indole compound of Formula (I) or pharmaceutically acceptable salt(s) thereof and process for the preparation thereof. The present invention also relates to a pharmaceutical composition of indole compound of Formula (I) or pharmaceutically acceptable salt(s) thereof for treating mycobacterial infection or antimalarial infection or antifungal infection in a subject in need thereof.

BACKGROUND AND PRIOR ART OF THE INVENTION

Tuberculosis (TB) is a disease that still challenges mankind by defying a comprehensive remedy. According to World Health Organization (WHO) report in 2016, 10.4 million people were afflicted with TB, and 1.7 million died from the disease. Over 95% of TB deaths occur under developed and developing countries. Seven countries account for 64% of the total deaths due to TB, with India leading the count, followed by Indonesia, China, Philippines, Pakistan, Nigeria, and South Africa. Multidrug-resistant tuberculosis (MDR-TB) is a form of TB caused by bacteria that does not respond to, at least, isoniazid and rifampicin, the two most powerful, first-line (or standard) anti-TB drugs.

Article titled "Indole-2-carboxamide-based MmpL3 inhibitors show exceptional antitubercular activity in an animal model of tuberculosis infection" by J Stec et al. published in *J. Med. Chem.*, 2016, 59 (13), pp 6232-6247 reports the SAR of, 4,6-difluoro-N-((1R,2R,3R,5S)-2,6,6-trimethylbicyclo[3.1.1]heptan-3-yl)-1H-indole-2-carboxamide, that shows excellent activity against drug-sensitive (MIC=0.012 µM; SI≥16000), multidrug-resistant (MDR), and extensively drug-resistant (XDR) *Mycobacterium tuberculosis* strains, has superior ADMET properties, and shows excellent activity in the TB aerosol lung infection model.

The reported indole compounds are observed to possess potent anti-tubercular activity. Some of the compounds are found to have MIC in nM concentration ranges, but are highly lipophilic in nature and possessed low aqueous solubility. Therefore, a special delivery micro emulsion pre concentrate (MEPC) formulation is used to address the solubility limitation of the lead compounds for oral dosing. Thus, while remedies could have been made available to overcome issues of treatment of TB with novel, potent molecules that could address the vexed problem of multi-drug resistance, the indole compounds do not possess properties that will aid in formulating and delivering the drug to the site of action.

Therefore, there is a need to provide robust drug compound(s) for treatment of mycobacterial/fungal/malarial infection, process for its preparation and pharmaceutical composition thereof.

OBJECTS OF THE INVENTION

The main objective of the present invention is to provide a novel indole compound of Formula (I) or pharmaceutically acceptable salt(s) thereof.

Another objective of the present invention is to provide a process for the preparation of indole compound(s) of Formula (I) or pharmaceutically acceptable salt(s) thereof.

Yet another objective of the present invention is to provide a pharmaceutical composition comprising a compound of Formula (I), or a stereoisomer, or ester or pharmaceutically acceptable salt thereof and a pharmaceutically acceptable carrier, diluent or excipient for treating mycobacterial infection or antimalarial infection or antifungal infection in a subject in need thereof.

SUMMARY OF THE INVENTION

Accordingly, the present invention provides indole compound(s) of Formula (I) or pharmaceutically acceptable salt thereof,

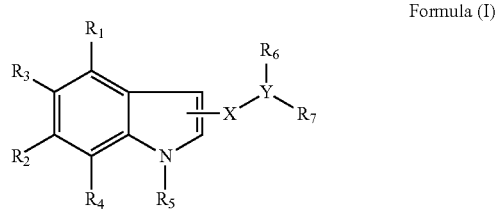

Formula (I)

Wherein;

X is selected from the group consisting of $CH_2$, —CO, —CONH, —CS or —CSNH;

Y is selected from the group consisting of —CH, or —NH, —N—

$R_1$, $R_2$, $R_3$, $R_4$, $R_5$ are same or different and each is independently selected from the group consisting of hydrogen, alkyl (linear and branched), cycloalkyl, aryl, heterocyclyl, heteroaryl, alkyl cycloalkyl, alkylaryl, alkylheterocyclyl, alkyl heteroaryl, alkenyl, halogen, trifluromethyl, nitro, amide, ester, cyano, alkoxy, alkylamino, arylamino;

$R_6$ and $R_7$ is selected from hydrogen, alkyl, alkyl containing at least one Si atom, substituted or unsubstituted cycloalkyl, substituted or unsubstituted cycloalkyl containing at least one —Si— atom, substituted or unsubstituted cycloalkyl containing at least one heteroatom, substituted or unsubstituted cycloalkyl containing at least one —Si— atom and at least one heteroatom;

$R_6$ and $R_7$ together form a cyclic ring may optionally containing at least one —Si— atom.

Provided that when $R_6$ and $R_7$ contain Si then X=CONH and Y=N.

Another embodiment of the present invention provides a process for the preparation of indole compounds (a-n) of Formula (I) comprising adding coupling agent to a solution of indole carboxylic acid and amine in a suitable solvent followed by stirring the reaction mixture for the period of 10 to 18 h at temperature in the range of 25 to 35° C. to afford compounds (a-n) of Formula (I).

Still another embodiment of the present invention provides a process for the preparation of indole compounds (o-bb) of Formula (I) comprising refluxing compound of Formula 1 with $SOCl_2$ followed by reacting with hydrazine hydrate in a suitable solvent at a suitable temperature for a suitable period of time to afford compound of Formula (o). And further reacting the compound of Formula (o) with alkyl/alkenyl halide RX' of Formula (3) in the presence of base and suitable solvent at a suitable temperature for a suitable period of time to obtain compounds (o-bb) of Formula (I).

Yet another embodiment of the present invention provides a pharmaceutical composition comprising a compound of Formula (I), or a stereoisomer, or ester or pharmaceutically acceptable salt(s) thereof and a pharmaceutically acceptable carrier, diluent or excipient.

Still another embodiment of the present invention provides a method for treating mycobacterial infection or antimalarial infection or antifungal infection in a subject in need thereof, comprising administering to the said subject a therapeutically effective amount of the compound of formula (I) or a pharmaceutically acceptable salt thereof.

DETAILED DESCRIPTION OF THE INVENTION

The invention will now be described in detail in connection with certain preferred and optional embodiments, so that various aspects thereof may be more fully understood and appreciated.

The term "alkyl" means a saturated straight or branched $C_1$-$C_{20}$ hydrocarbon group which include substituted and unsubstituted alkyl groups methyl, ethyl, propyl, isopropyl, butyl, isobutyl, t-butyl, pentyl, isopentyl, neopentyl, hexyl, heptyl, octyl, 2-methyl-1-propyl, 2-chloro-2-propyl, 2-bromo-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl.

The term "aryl" means a carbocyclic single or multiple aromatic ring system which include phenyl, tolyl, anthracenyl, fluorenyl, indenyl, and naphthyl. The aromatic ring can be substituted at least one ring position with substituents that include, e.g., alkanoyl, alkoxy, alkyl, alkenyl, alkynyl, amido, amidino, amino, aryl, arylalkyl, azido, azo, carbamate, carbamide, carbonate, carbonyl, carboxy, cyano, cycloalkyl, ester, ether, formyl, halogen, haloalkyl, heteroaryl, heterocyclyl, hydrazine, hydroxyl, imino, ketone, nitro, sulfate, sulfide, sulfonamido, sulfonyl and thiocarbonyl. The term "aryl" also includes polycyclic ring systems having at least two cyclic rings in which at least two carbons are common to two adjoining rings (the rings are "fused rings") wherein at least one of the rings is aromatic, e.g., the other cyclic rings can be cycloalkyls, cycloalkenyls, cycloalkynyls, aryls, and combinations thereof.

The terms "halo" and "halogen" mean fluorine, chlorine, bromine or iodine.

The term 'cycloalkyl' means $C_1$ to $C_8$ saturated cyclic rings which may be substituted or unsubstituted.

Whenever the term "substituted" is used in the present invention, it is meant to indicate that one or more hydrogen on the atom indicated in the expression using "substituted" is replaced with a selection from the indicated group, provided that the indication atom's normal valence is not exceeded, and that the substitution results in a chemically stable compound, i.e. a compound that is sufficiently robust to survive isolation to a useful degree of purity from a reaction mixture. Unless otherwise mentioned, when the term "substituted" is used, it refers to one or more substituents selected from the group consisting of halogen, hydroxyl, nitro, cyano, thiocyanate, cyanamide, amido, thioamido, sulfonamide, $C_1$-$C_{50}$ alkyl, $C_2$-$C_{50}$ alkenyl, $C_2$-$C_{50}$ alkynyl, $C_3$-$C_{50}$ cycloalkyl, ester, thioester, dithioester, ether, thioether, $C_6$-$C_{15}$ aryl, heterocycle, peroxide, oxy derivative, thio derivative, acyl derivative, thioketone, sulfonyl derivative or sulfinyl derivative, thiol, nitrate, phosphate ester, thiophosphate ester, sulfate ester, carboxylic acid, phosphonic acid, phosphinic acid, sulfonic acid, amino, ammonium, imine, oxime, diazo, and hydroxamic acid.

In the view of above, the present invention provides an indole compound of Formula (I) or pharmaceutically acceptable salt thereof, process for the preparation thereof and use thereof for treating mycobacterial infection or antimalarial infection or antifungal infection. The present invention further provides a pharmaceutical composition comprising a compound of Formula (I), or a stereoisomer, or ester or pharmaceutically acceptable salt thereof and a pharmaceutically acceptable carrier, diluent or excipient.

In an embodiment, the present invention provides indole compound of Formula (I) or pharmaceutically acceptable salt thereof,

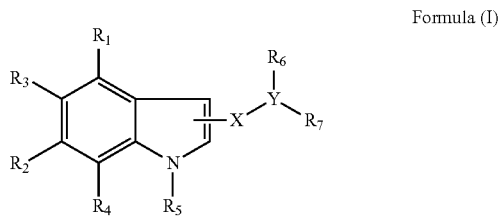

Formula (I)

wherein,

X is selected from the group consisting of $CH_2$, —CO, —CONH, —CS or —CSNH;

Y is selected from the group consisting of —CH, or —NH, —N—;

$R_1$, $R_2$, $R_3$, $R_4$, $R_5$ are same or different and each is independently selected from the group consisting of hydrogen, alkyl (linear and branched), cycloalkyl, aryl, heterocyclyl, heteroaryl, alkyl cycloalkyl, alkylaryl, alkylheterocyclyl, alkyl heteroaryl, alkenyl, halogen, trifluromethyl, nitro, amide, ester, cyano, alkoxy, alkylamino, arylamino;

$R_6$ and $R_7$ is selected from hydrogen, alkyl, alkyl containing at least one Si atom, substituted or unsubstituted cycloalkyl, substituted or unsubstituted cycloalkyl containing at least one —Si— atom, substituted or unsubstituted cycloalkyl containing at least one heteroatom, substituted or unsubstituted cycloalkyl containing at least one —Si— atom and at least one heteroatom;

$R_6$ and $R_7$ together form a cyclic ring may optionally containing at least one —Si— atom, Provided that when $R_6$ and $R_7$ contain Si then X=CONH and Y=N.

In particularly preferred embodiment, the compound of Formula (I) is selected from the group comprising of.

i. N-(4, 4-dimethylcyclohexyl)-1H-indole-2-carboxamide (a);
ii. N-(1, 1-dimethylsilinan-4-yl)-1H-indole-2-carboxamide (b);
iii. (4, 4-dimethyl-1,4-azasilinan-1-yl)-1H-indole-2-carboxamide (c);
iv. (4, 4-dimethyl-1,4-azasilinan-1-yl)(1H-indol-2-yl) methanone (d);
v. 4, 6-dichloro-N-(1,1-dimethylsilinan-4-yl)-1H-indole-2-carboxamide (e);
vi. 4, 6-dichloro-N-(4,4-dimethyl-1,4-azasilinan-1-yl)-1H-indole-2-carboxamide (f);
vii. (4, 6-dichloro-1H-indol-2-yl)(4,4-dimethyl-1,4-azasilinan-1-yl)methanone (g);
viii. 4, 6-dichloro-N-(4,4-dimethylpiperidin-1-yl)-1H-indole-2-carboxamide (h);
ix. N-(1,1-dimethylsilinan-4-yl)-4,6-difluoro-1H-indole-2-carboxamide (i);
x. N-(4, 4-dimethyl-1,4-azasilinan-1-yl)-4,6-difluoro-1H-indole-2-carboxamide (j);

xi. (4, 6-difluoro-1H-indol-2-yl)(4,4-dimethyl-1,4-azasilinan-1-yl)methanone (k);
xii. N-(4, 4-dimethylpiperidin-1-yl)-4, 6-difluoro-1H-indole-2-carboxamide (l).
xiii. 4,6-dichloro-N-(4,4-dimethyl-1,4-azasilinan-1-yl)-1H-indole-2-carboxamide hydrochloride (m)
xiv. 4,6-dichloro-N-(4,4-dimethylpiperidin-1-yl)-1H-indole-2-carboxamide hydrochloride (n)
xv. 1H-indole-2-carbohydrazide (o)
xvi. N',N'-diethyl-1H-indole-2-carbohydrazide (p)
xvii. N',N'-dibutyl-1H-indole-2-carbohydrazide (q)
xviii. N',N'-dipentyl-1H-indole-2-carbohydrazide (r)
xix. N',N'-dihexyl-1H-indole-2-carbohydrazide (s)
xx. N-(piperidin-1-yl)-1H-indole-2-carboxamide (t)
xxi. N',N'-diallyl-1H-indole-2-carbohydrazide (u)
xxii. 4,6-dichloro-1H-indole-2-carbohydrazide (v)
xxiii. 4,6-dichloro-N',N'-diethyl-1H-indole-2-carbohydrazide (w)
xxiv. N',N'-dibutyl-4,6-dichloro-1H-indole-2-carbohydrazide (x)
xxv. 4,6-dichloro-N',N'-dipentyl-1H-indole-2-carbohydrazide (y)
xxvi. 4,6-dichloro-N',N'-dihexyl-1H-indole-2-carbohydrazide (z)
xxvii. 4,6-dichloro-N-(piperidin-1-yl)-1H-indole-2-carboxamide (aa)
xxviii. N',N'-diallyl-4,6-dichloro-1H-indole-2-carbohydrazide (bb)

Another embodiment of the present invention provides a process for the preparation of indole compound of Formula (I) as depicted in scheme-1 below for the compounds (a-n), wherein the process comprises of adding coupling agent to a solution of indole compound of Formula 1 and amine of Formula 2 in a suitable solvent followed by stirring the reaction mixture for the period of 10 to 18 h at temperature in the range of 25 to 35° C. to afford compound of Formula (I).

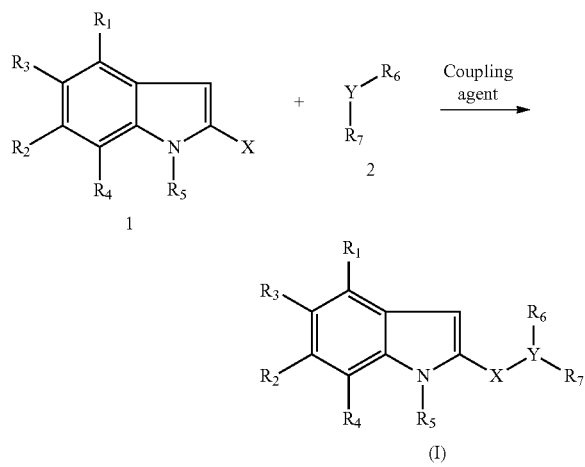

Scheme 1 wherein,
X is selected from the group consisting of —CH$_2$, —CO, —CONH, —CS, or CSNH;
Y is selected from the group consisting of —CH, or —NH, —N—;
$R_1$, $R_2$, $R_3$, $R_4$, $R_5$ are same or different and each is independently selected from the group consisting of hydrogen, alkyl (linear and branched), cycloalkyl, aryl, heterocyclyl, heteroaryl, alkylcycloalkyl, alkylaryl, alkylheterocyclyl, alkylheteroaryl, alkenyl, halogen, trifluromethyl, nitro, amide, ester, cyano, alkoxy, alkylamino, arylamino;

$R_6$ and $R_7$ is selected from hydrogen, alkyl, alkyl containing at least one Si atom, substituted or unsubstituted cycloalkyl, substituted or unsubstituted cycloalkyl containing at least one —Si— atom, substituted or unsubstituted cycloalkyl containing at least one heteroatom, substituted or unsubstituted cycloalkyl containing at least one —Si— atom and at least one heteroatom;

$R_6$ and $R_7$ together form a cyclic ring may optionally containing at least one —Si— atom, Provided that when $R_6$ and $R_7$ contain Si then X=CONH and Y=N.

Compound of Formula 1 is selected from 1H-indole-2carboxylic acid, 4,6-dichloro-1H-indole-2carboxylic acid or 4,6-difluoro-1H-indole-2carboxylic acid.

The amine compound of Formula 2 is selected from 4,4-dimethylcyclohexan-1-amine, 1,1-dimethylsilinan-4-amine, 4,4-dimethyl-1,4-azasilinan-1-amine, 4,4-dimethylpiperidin-1-amine, 4,4-dimethyl-1,4-azasilinane.

The coupling agent is selected from N-(3-Dimethylaminopropyl)-N'-ethylcarbodiimide hydrochloride (EDCCl), 1-hydroxybenzotriazole (HOBt), N, N-diisopropylethylamine (DIPEA) or (1-[Bis(dimethylamino)methylene]-1H-1,2,3-triazolo[4,5-b]pyridinium 3-oxid hexafluorophosphate [Hexafluorophosphate Azabenzotriazole Tetramethyl Uronium (HATU)] or mixture thereof. In particularly preferred embodiment, HOBt and DIPEA is used.

Suitable solvent for the reaction may include the polar solvents, non-polar solvents, alcohol solvents, ether solvents, ester solvents, and the mixtures thereof. Polar solvents may include water, ammonia, sulfuric acid, deuterium oxide, ethanol, methanol, acetone, isopropanol, methyl ethyl ketone, n-propanol, acetonitrile, DMSO, and dimethyl formamide (DMF) and mixtures thereof. Non-polar solvents may include chloroform, pentane, hexane, benzene, toluene, octane, decane, dimethyl ether, and dichloromethane, and mixtures thereof. Alcohol solvents may include methanol, ethanol, isopropanol, and mixtures thereof. Ether solvents may include tetrahydrofuran, diethyl ether, 1,4-dioxane, methyl tert-butyl ether, and mixtures thereof. Ester solvents may include methyl acetate, ethyl acetate, isopropyl acetate, tert-butyl acetate, and mixtures thereof. In particularly, polar solvents are used and most preferably DMF is used in the reaction.

In one embodiment of the invention, the present invention provides a pharmaceutical composition comprising a compound of formula (I), or a stereoisomer, or ester or pharmaceutically acceptable salt thereof and a pharmaceutically acceptable carrier, diluent or excipient.

Suitable period of time to conduct the reaction is 10-14 hours, most preferably period of time is 14 hours.

Suitable temperature to conduct the reaction is in the range of 25-35° C. In a preferred embodiment, suitable temperature is 35° C.

Yet another embodiment of the present invention is to provide process for the preparation of compound of Formula (I), i.e., compounds (o-bb) as depicted below in scheme-2, wherein said process comprises of:
a) refluxing the compound of Formula 1 with thionyl chloride (SOCl$_2$) for a suitable period of time at a suitable temperature followed by reacting the obtained crude compound with hydrazine hydrate in a suitable solvent for a suitable period of time at a suitable temperature to afford an intermediate compound;

b) optionally, reacting the intermediate compound with alkyl/alkenyl halide RX' compounds of Formula 3 in the presence of suitable base in a suitable solvent for the suitable period of time at a suitable temperature to afford compound of Formula (I), i.e., compounds (o-bb).

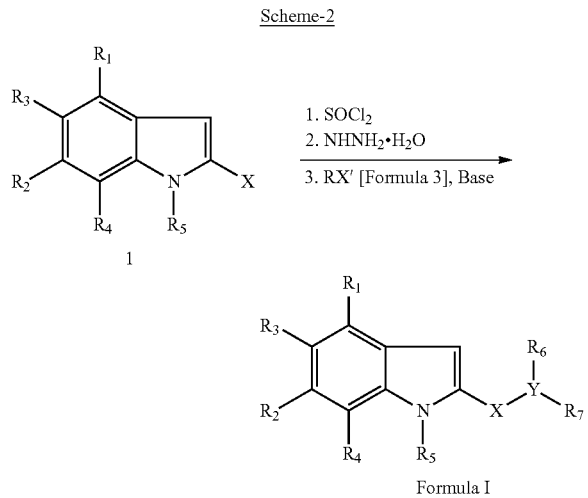

Scheme-2

Formula I wherein,

Compound of Formula 1 is as defined above and RX' is $C_2$-$C_{12}$ alkyl or $C_2$-$C_{12}$ alkenyl halides or aralakyl halides and which may have further substitution. Most preferably, the halide compounds of Formula 3 is elected from ethyl, n-propyl, n-butyl, n-pentyl, n-hexyl halides or 1,5-dihalopenatane, or bis-1,2-xylyl halides.

Suitable period of time for refluxing the crude compound in step a) is 1-2 h. In a preferred embodiment, suitable period of time is 2 hour.

Suitable temperature in step a) to obtain crude compound is in the range of 80° C.-100° C. and in a preferred embodiment, the temperature is 100° C.

Suitable solvent in step a) may include the polar solvents, non-polar solvents, alcohol solvents, ether solvents, ester solvents, and the mixtures thereof. Polar solvents may include water, ammonia, sulfuric acid, deuterium oxide, ethanol, methanol, acetone, isopropanol, methyl ethyl ketone, n-propanol, acetonitrile, DMSO, and dimethyl formamide (DMF) and mixtures thereof. Non-polar solvents may include chloroform, pentane, hexane, benzene, toluene, octane, decane, dimethyl ether, and dichloromethane, and mixtures thereof. Alcohol solvents may include methanol, ethanol, isopropanol, and mixtures thereof. Ether solvents may include tetrahydrofuran, diethyl ether, 1,4-dioxane, methyl tert-butyl ether, and mixtures thereof. Ester solvents may include methyl acetate, ethyl acetate, isopropyl acetate, tert-butyl acetate, and mixtures thereof. In a particular useful embodiments, alcohol solvents are used and most preferably ethanol is used in a reaction.

Suitable period of time to obtain the compound of Formula (o) in step a) is 1-2 h. In a preferred embodiment, suitable period of time is 2 hours.

Suitable temperature in step a) to obtain the compound of Formula (o) is in the range of 80-100° C. and more particularly 100° C.

Suitable base used in step b) includes but not limited to sodium carbonate, potassium carbonate, sodium hydroxide, potassium hydroxide, sodium bicarbonate, potassium bicarbonate. In a preferred embodiment, potassium carbonate is used.

Suitable period of time to conduct the reaction in step b) is 10-12 hours. In a preferred embodiment, suitable period of time at step b) is 12 hours.

Suitable temperature in step b) is in the range of 95–105° C. In a preferred embodiment, suitable temperature in step b) is 100° C.

Suitable solvent for the reaction in step b) include but not limited to the polar solvents, non-polar solvents, alcohol solvents, ether solvents, ester solvents, and the mixtures thereof. Polar solvents include but not limited to water, ammonia, sulfuric acid, deuterium oxide, ethanol, methanol, acetone, isopropanol, methyl ethyl ketone, n-propanol, acetonitrile, DMSO, and dimethyl formamide (DMF) and mixtures thereof. Non-polar solvents include but not limited to chloroform, pentane, hexane, benzene, toluene, octane, decane, dimethyl ether, and dichloromethane, and mixtures thereof. Alcohol solvents include but not limited to methanol, ethanol, isopropanol, and mixtures thereof. Ether solvents include but not limited to tetrahydrofuran, diethyl ether, 1,4-dioxane, methyl tert-butyl ether, and mixtures thereof. Ester solvents include but not limited to methyl acetate, ethyl acetate, isopropyl acetate, tert-butyl acetate, and mixtures thereof. In a particular useful embodiment, polar solvents are used and most preferably DMF is used in the reaction.

The compound of Formula (I) or pharmaceutically acceptable salt(s) thereof as disclosed herein is present in the composition in an amount which is effective to treat the disease or the condition caused by the mycobacterial/fungal/malarial strains. The pharmaceutical compositions of the invention can be prepared by combining a compound of the invention with appropriate pharmaceutically acceptable carriers, diluents or excipient or vehicles and may be formulated into preparations in solid, semi-solid, liquid or gaseous forms, such as tablets, capsules, powders, granules, ointments, solutions, injections, gels and microspheres.

Accordingly, the pharmaceutical compositions containing compound of Formula (I) may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

Pharmaceutical compositions of the invention are formulated so as to allow the active ingredients contained therein to be bioavailable upon administration of the composition to a patient. Compositions that will be administered to a subject or patient may take the form of one or more dosage units. The dosage forms can also be prepared as sustained, controlled, modified and immediate dosage forms.

In still another embodiments, the present invention provides a method for treating mycobacterial infection or in a subject in need thereof; comprising administering to the said subject a therapeutically effective amount of the compound of Formula (I) or a pharmaceutically acceptable salt thereof.

From the anti-*Mycobacterium tuberculosis* activity data of the compounds against Mtb. H37Rv, it is observed that the minimum inhibitory concentration (MIC) of the indole compounds of formula (I) of the instant invention are comparable with that of standard used [NITD 304 (Standard) and NITD 349 (Standard)].

In still another embodiments, the present invention provides a method for treating mycobacterial infection or antimalarial infection or antifungal infection in a subject in need thereof, comprising administering to the said subject a therapeutically effective amount of the compound of Formula (I) or a pharmaceutically acceptable salt thereof.

The pharmaceutical composition comprising compound of Formula (I) is used to treat mycobacterial infections with improved physico-chemical properties, in particular lipophilicity and in vivo metabolism. This may lead to drug candidates with improved brain penetration and better safety profile.

The invention further provides a method of treating mycobacterial infection in a subject infected with *Mycobacterium* employing the compound of Formula (I), alone or in combination with compounds reported for anti-tubercular activity. The compound may be administered alone or in combination with known or approved anti-mycobacterial drugs selected from, but not limited to streptomycin, rifampicin, isoniazid, pyrazinamide and ethambutol.

Anti-*Mycobacterium Tuberculosis* Activity of the Synthesized Indole Compounds of Formula (I):

Anti-*Mycobacterium Tuberculosis* Assay Protocol:

Growth Media & Reagents

All bacterial media and supplements including Middlebrook 7H9 broth; Middlebrook 7H11 Agar; albumin, dextrose and catalase supplement; oleic acid, albumin, dextrose and catalase (OADC) supplement are purchased from Becton-Dickinson (NJ, USA). All the other chemicals and antibiotics are procured from Sigma-Aldrich (MO, USA).

Bacterial Cultures & Cell Line

The bacterial strains utilized are drug susceptible *M. tuberculosis* H37Rv ATCC 27294, INH-resistant *M. tuberculosis* ATCC 35822, RIF-resistant *M. tuberculosis* ATCC 35838, streptomycin (STR)-resistant *M. tuberculosis* ATCC 35820 and ETB-resistant *M. tuberculosis* ATCC 35837. All bacterial strains are procured from ATCC (ATCC, VA, USA). The mycobacteria are propagated in Middlebrook 7H9 broth supplemented with glycerol, albumin, dextrose and catalase and 0.05% Tween-80 at 37° C.

Antibacterial Susceptibility Testing

Antibacterial susceptibility testing is carried out utilizing broth microdilution assay according to CLSI guidelines. Results are summarized below in Table 1. A total of 10 mg/ml stock solutions of test and control compounds are prepared in DMSO and stored in −20° C. Bacterial cultures are inoculated in appropriate media and optical density (OD) 600 of the cultures is measured, followed by dilution to achieve ~$10^6$ colony-forming units (CFU)/mL. The compounds are tested from 64 to 0.5 µg/ml in twofold serial diluted fashion with 2.5 µl of each compound added per well of a 96-well round bottom microtiter plate. Later, 97.5 µl of ~$10^6$ CFU/ml bacterial suspension is added to each well containing the test compound along with appropriate controls. The plates are incubated at 37° C. for 7 days for *M. tuberculosis*. The MIC is defined as the lowest compound concentration where there is no visible growth. For each compound, MIC determinations are carried independently three-times in duplicate.

TABLE 1

| Compound | MIC against *mycobacterium tuberculosis* Mtb. H37Rv |
|---|---|
| Compound (a) | 0.06 µg/mL |
| Compound (b) | 0.03 µg/mL |
| Compound (c) | 2.0 µg/mL |
| Compound (d) | 32 µg/mL |

TABLE 1-continued

| Compound | MIC against *mycobacterium tuberculosis* Mtb. H37Rv |
|---|---|
| Compound (e) | 0.03 µg/mL |
| Compound (f) | 0.03 µg/mL |
| Compound (g) | 16.0 µg/mL |
| Compound (h) | ND |
| Compound (i) | 0.03 µg/mL |
| Compound (j) | 0.125 µg/mL |
| Compound (k) | 32.0 µg/mL |
| Compound (l) | ND |
| Compound (m) | ND |
| Compound (n) | ND |
| Compound (o) | ND |
| Compound (p) | ND |
| Compound (q) | ND |
| Compound (r) | ND |
| Compound (s) | ND |
| Compound (t) | ND |
| Compound (u) | ND |
| Compound (v) | ND |
| Compound (w) | ND |
| Compound (x) | ND |
| Compound (y) | ND |
| Compound (z) | ND |
| Compound (aa) | ND |
| Compound (bb) | ND |
| NITD 304 (Standard) | 0.06 µg/mL |
| NITD 349 (Standard) | 0.03 µg/mL |

In Vitro Solubility of the Active Compounds:

10 µM of standard solution is prepared in DMSO, 5 µM of working solution is prepared in DMSO from the standard solution. 495 µL of Buffer (1.2, 2.2, 4.5, 7.4 and 10.2 pH) is transferred in a pre labelled micro centrifuge tube. 5 µL of working solution (5 µM) is added in to the test system. Samples are Vortexed in a table top vortexer for 5 min and centrifuged at 14000 RPM for 5 minutes; supernatant samples are subjected to HPLC analysis. Results are summarized below in Table 2.

TABLE 2

| | Solubility in µM | | | | |
|---|---|---|---|---|---|
| Compound | pH 1.2 | pH 2.2 | pH 4.5 | pH 7.4 | pH 10.2 |
| Compound (f) | 40.42 | 26.29 | 2.57 | 2.57 | 2.70 |
| Compound (j) | 49.71 | 31.26 | 1.01 | 1.00 | 1.10 |
| Compound (i) | 0.00 | 0.00 | 0.00 | 0.00 | 9.03 |
| NITD 349 | 0.24 | 0.29 | 0.15 | 0.24 | 7.30 |
| Compound (h) | 41.07 | 30.03 | 8.60 | 6.32 | 8.67 |
| Compound (l) | 49.62 | 46.38 | 17.29 | 29.40 | 21.37 |
| Compound (m) | 38.60 | 28.44 | 2.55 | 2.73 | 2.46 |
| Compound (n) | 42.58 | 26.19 | 7.24 | 10.58 | 9.89 |
| NITD 304 | Insoluble in DMSO @ 10 µM Concentration. | | | | |
| Compound (e) | Solubility Experiment not performed. | | | | |

To overcome the aqueous solubility issue, the present invention is primarily focused on modifying the cyclohexyl moieties so as to improve Mtb activity as well as other PK properties. It is observed that, the Compound 6, 8, 10, 12, and HCl salts 13 and 14 showed good aqueous solubility at the acidic pH.

EXAMPLES

Following examples are given by way of illustration and therefore should not be construed to limit the scope of the invention.

Example A: General Procedure by Using Indole Carboxylic Acid Derivatives for the Synthesis of Compound of Formula (I)

To a solution of indole carboxylic acid compound of Formula 1 (1 eq) and amine compound (RNH$_2$) of Formula 2 (1.2 eq) in dry DMF (5 mL) EDC·HCl (1.2 eq), HOBt (2.2 eq), DIPEA (6 eq) were added and stirred for 14 h at 35° C. The reaction mixture was diluted with water (10 mL), extracted with Ethyl acetate (15 mL×3), saturated aq. NaHCO$_3$ solution (10 mL×2) and dried over anhydrous Na$_2$SO$_4$ concentrate in vacuum. The crude material obtained after removal of solvent was purified by column chromatography to obtain pure material.

Example 1: N-(4,4-dimethylcyclohexyl)-1H-indole-2-carboxamide (a)

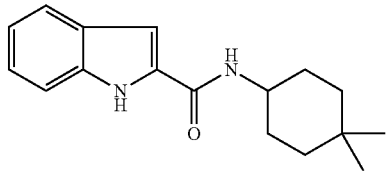

Compound (a)

To a solution of indole carboxylic acid (1 eq) and 4,4-dimethylcyclohexan-1-amine (1.2 eq) in dry DMF (5 mL) EDC·HCl (1.2 eq), HOBt (2.2 eq), DIPEA (6 eq) were added and stirred for 14 h at 35° C. The reaction mixture was diluted with water (10 mL), extracted with Ethyl acetate (15 mL×3), saturated aq. NaHCO$_3$ solution (10 mL×2) and dried over anhydrous Na$_2$SO$_4$ concentrate in vacuum. The crude material obtained after removal of solvent was purified by column chromatography to obtain pure material.

White solid product (38 mg, 42% yield); $^1$H NMR (400 MHz, CHLOROFORM-d) δ=9.84 (br. s., 1H), 7.61 (d, J=7.3 Hz, 1H), 7.42 (d, J=7.9 Hz, 1H), 7.24 (d, J=6.7 Hz, 1H), 7.11 (t, J=7.3 Hz, 1H), 6.81 (br. s., 1H), 6.11 (d, J=6.7 Hz, 1H), 4.02-3.89 (m, 1H), 1.96-1.86 (m, 2H), 1.54-1.28 (m, 6H), 0.94 (s, 6H); $^{13}$C NMR (101 MHz, CHLOROFORM-d) δ=161.0, 136.4, 131.1, 127.6, 124.2, 121.8, 120.5, 112.0, 101.5, 48.8, 37.6, 31.6, 28.9, 25.0; HRMS (ESI): m/z calculated for C$_{17}$H$_{22}$ON$_2$Na [M+Na]$^+$ 293.1624 found 293.1611.

Example 2: N-(1,1-dimethylsilinan-4-yl)-1H-indole-2-carboxamide (b)

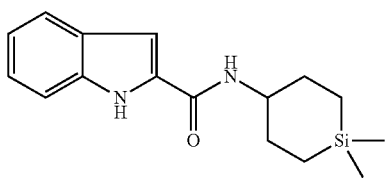

Compound (b)

White solid product (48 mg, 54% yield); $^1$H NMR (400 MHz, CDCl$_3$) δ 10.58 (br. s., 1H), 8.01 (d, J=7.9 Hz, 1H), 7.85 (d, J=7.9 Hz, 1H), 7.65 (t, J=7.3 Hz, 1H), 7.50 (t, J=7.3 Hz, 1H), 7.21 (s, 1H), 6.59 (d, J=7.9 Hz, 1H), 4.36 (d, J=8.5 Hz, 1H), 2.67-2.53 (m, 2H), 2.27-1.84 (m, 2H), 1.21-1.10 (m, 4H), 0.47 (s, 3H), 0.44 (s, 3H); $^{13}$C NMR (100 MHz, CDCl$_3$) δ 160.8, 136.5, 131.1, 127.5, 124.1, 121.7, 120.4, 112.1, 101.5, 51.0, 30.7, 11.7, −2.7, −4.3; HRMS (ESI): m/z calculated for C$_{16}$H$_{23}$ON$_2$Si[M+H]$^+$ 287.1574 found 287.1612.

Example 3: N-(4,4-dimethyl-1,4-azasilinan-1-yl)-1H-indole-2-carboxamide (c)

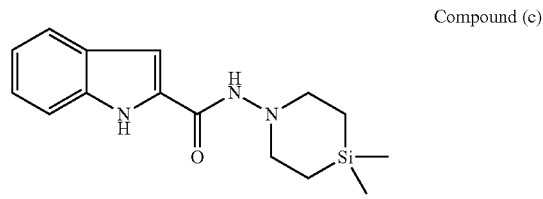 [SMILES: C[Si]1(C)CCN(NC(=O)c2cc3ccccc3[nH]2)CC1]

Compound (c)

White solid product (72 mg, 81% yield); $^1$H NMR: $^1$H NMR (400 MHz, CDCl$_3$) δ 9.73 (br. s., 1H), 7.73 (d, J=7.3 Hz, 1H), 7.64 (br. s., 1H), 7.45 (br. s., 1H), 7.33-7.29 (m, 1H), 7.14 (br. s., 1H), 3.51-3.33 (m, 1H), 3.21 (br. s., 2H), 2.90 (br. s., 1H), 0.98 (br. s., 4H), 0.19-0.12 (m, 6H); $^{13}$C NMR (100 MHz, CDCl$_3$) δ 162.1, 135.9, 128.9, 127.5, 124.8, 122.5, 121.8, 120.6, 112.0, 109.5, 101.7, 55.6, 12.9, −3.50; HRMS (ESI): m/z calculated for C$_{15}$H$_{22}$ON$_3$Si[M+H]$^+$ 288.1527 found 288.1541.

Example 4: (4,4-dimethyl-1,4-azasilinan-1-yl)(1H-indol-2-yl)methanone (d)

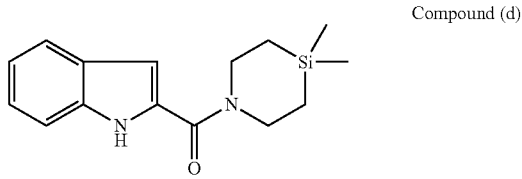 [SMILES: C[Si]1(C)CCN(C(=O)c2cc3ccccc3[nH]2)CC1]

Compound (d)

White solid product (69 mg, 82% yield); $^1$H NMR (400 MHz, CDCl$_3$) δ 9.83 (br. s., 1H), 7.68 (d, J=7.9 Hz, 1H), 7.47 (d, J=8.5 Hz, 1H), 7.36-7.24 (m, 1H), 7.24-7.09 (m, 1H), 6.92 (s, 1H), 4.06 (br. s., 4H), 1.01 (br. s., 4H), 0.19 (s, 6H); $^{13}$C NMR (100 MHz, CDCl$_3$) δ 162.0, 135.6, 129.7, 127.7, 124.1, 121.7, 120.3, 111.8, 104.3, 46.5, 43.4, 15.0, 14.1, −3.0; HRMS (ESI): m/z calculated for C$_{15}$H$_{21}$ON$_2$Si [M+H]$^+$ 273.1418 found 273.1422.

Example 5: 4,6-dichloro-N-(1,1-dimethylsilinan-4-yl)-1H-indole-2-carboxamide (e)

Compound (e)

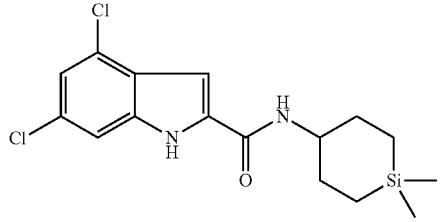

White solid product (90 mg, 58% yield); $^1$H NMR (400 MHz, DMSO-d$_6$) δ 12.03 (br. s., 1H), 8.45 (br. s., 1H), 7.41 (br. s., 1H), 7.29 (br. s., 1H), 7.20 (br. s., 1H), 3.71 (br. s., 1H), 1.98 (br. s., 2H), 1.59 (d, J=11.6 Hz, 2H), 0.78-0.75 (m, 2H), 0.63-0.60 (m, 2H), 0.08 (br. s., 3H), 0.02 (br. s., 3H); $^{13}$C NMR (100 MHz, DMSO-d$_6$) δ 158.9, 136.7, 133.8, 127.5, 126.2, 124.8, 119.3, 111.1, 100.5, 50.5, 30.1, 11.7, −2.3, −4.5; HRMS (ESI): m/z calculated for $C_{16}H_{21}ON_2Cl_2Si[M+H]^+$ 355.0795 found 355.0805.

Example 6: 4,6-dichloro-N-(4,4-dimethyl-1,4-azasilinan-1-yl)-1H-indole-2-carboxamide (f)

Compound (f)

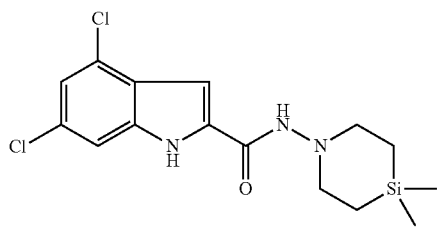

White solid product (102 mg, 82% yield); $^1$H NMR: $^1$H NMR (500 MHz, CDCl$_3$) δ □ 11.14 (br. d 1H) 7.76 (br. s., 1H), 7.42 (d, J=7.2 Hz, 1H), 7.11 (br. s., 1H), 6.91 (br. s., 1H), 3.41 (br. s., 1H), 3.24 (br. s., 2H), 2.94 (t, J=10.7 Hz, 1H), 1.11-1.03 (m, 1H), 1.03-0.92 (m, 4H), 0.16 (d, J=11.8 Hz, 3H), 0.11 (br. s., 3H); $^{13}$C NMR (125 MHz, CDCl3) δ 159.2, 137.1, 130.6, 129.6, 128.9, 128.0, 127.1, 125.3, 120.6, 111.0, 109.2, 108.0, 100.5, 55.6, 13.0, −3.6; HRMS (ESI): m/z calculated for $C_{15}H_{20}ON_3Cl_2Si[M+H]^+$ 356.0747 found 356.0759.

Example 7: (4,6-dichloro-1H-indol-2-yl)(4,4-dimethyl-1,4-azasilinan-1-yl)methanone (g)

Compound (g)

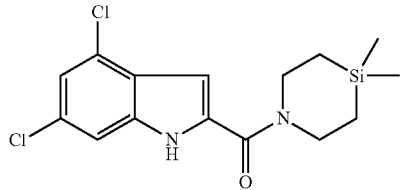

White solid product (64 mg, 43% yield); $^1$H NMR (400 MHz, CDCl$_3$) δ 10.80 (br. s., 1H), 7.37 (br. s., 2H), 7.13 (br. s., 1H), 6.92 (br. s., 1H), 4.10 (br. s., 2H), 4.04 (br. s., 2H), 1.03 (br. s., 4H), 0.20 (br. s., 6H); $^{13}$C NMR (100 MHz, CDCl$_3$) δ 161.5, 136.4, 130.8, 129.6, 129.0, 127.8, 127.3, 125.3, 120.6, 110.7, 102.7, 46.6, 43.7, 15.2, 14.1, −3.0; HRMS (ESI): m/z calculated for $C_{15}H_{19}ON_2Cl_2Si[M+H]^+$ 341.0638 found 341.0647.

Example 8: 4,6-dichloro-N-(4,4-dimethylpiperidin-1-yl)-1H-indole-2-carboxamide (h)

Compound (h)

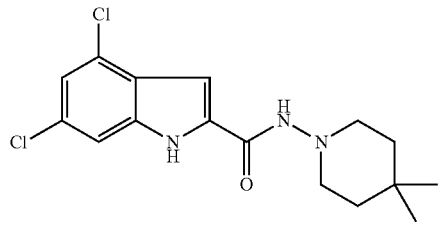

White solid product (18 mg, 41% yield); $^1$H NMR (500 MHz, CDCl$_3$) δ 10.25 (br. s., 1H), 10.14 (br. s., 1H), 7.39 (d, J=13.7 Hz, 1H), 7.16 (s, 1H), 6.92 (br. s., 1H), 6.79 (br. s., 1H), 3.10 (d, J=9.2 Hz, 1H), 2.94 (br. s., 2H), 2.69 (t, J=10.9 Hz, 1H), 1.75 (t, J=11.6 Hz, 2H), 1.53 (d, J=12.6 Hz, 2H), 1.02 (br. s., 6H).

Example 9: N-(1,1-dimethylsilinan-4-yl)-4,6-difluoro-1H-indole-2-carboxamide (i)

Compound (i)

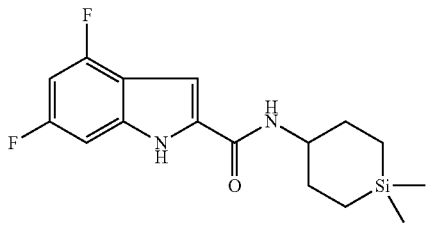

White solid product (31 mg, 34% yield); $^1$H NMR (400 MHz, DMSO-d$_6$) δ 11.93 (br. s., 1H), 7.25 (s, 1H), 7.01 (d, J=9.2 Hz, 1H), 6.86 (t, J=10.4 Hz, 1H), 3.70 (br. s., 1H), 2.00-1.97 (m, 2H), 1.59 (q, J=12.2 Hz, 2H), 0.77 (d, J=14.0 Hz, 2H), 0.61 (t, J=10.9 Hz, 1H), 0.08 (s, 3H), 0.03 (s, 3H); $^{13}$C NMR (100 MHz, DMSO-d$_6$) δ 158.9, 159.6 (dd, J=237.6, 11.6 Hz), 155.6 (dd, J=248.1, 15.4 Hz), 137.5 (t, J=13.9 Hz), 132.9 113.0 (d, J=22.3 Hz), 98.1, 95.0 (dd, J=29.2, 23.1 Hz), 94.5 (dd, J=26.2, 3.8 Hz), 50.3, 30.1, 11.7, −2.4, −4.5; HRMS (ESI): m/z calculated for $C_{16}H_{21}ON_2F_2Si[M+H]^+$ 323.1386 found 323.1394.

Example 10: N-(4,4-dimethyl-1,4-azasilinan-1-yl)-4,6-difluoro-1H-indole-2-carboxamide (j)

Compound (j)

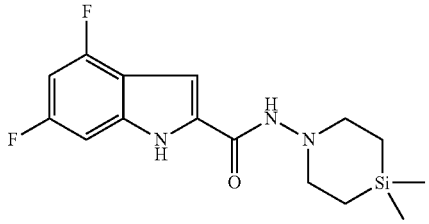

White solid product (28 mg, 32% yield); $^1$H NMR (400 MHz, CD$_3$OD) δ 7.13 (s, 1H), 6.99 (d, J=9.2 Hz, 1H), 6.64 (t, J=10.1 Hz, 1H), 3.11 (t, J=5.5 Hz, 4H), 0.96 (t, J=5.8 Hz, 4H), 0.10 (s, 6H); $^{13}$C NMR (100 MHz, CD$_3$OD) δ 160.9, 161.9 (dd, J=239.6, 12.3 Hz), 158.0 (dd, J=249.7, 15.4 Hz), 139.6 (t, J=14.6 Hz), 132.3, 115.1 (d, J=21.6 Hz), 99.9, 96.3 (dd, J=30.0, 23.9 Hz), 95.3 (dd, J=26.2, 4.6 Hz), 56.5, 14.4, −3.4; HRMS (ESI): m/z calculated for C$_{15}$H$_{20}$ON$_3$F$_2$Si[M+H]$^+$ 324.1338 found 324.1346.

Example 11: (4,6-difluoro-1H-indol-2-yl)(4,4-dimethyl-1,4-azasilinan-1-yl)methanone (k)

Compound (k)

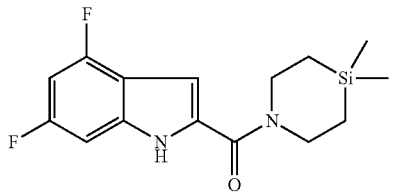

White solid product (69 mg, 82% yield); $^1$H NMR (400 MHz, CDCl$_3$) δ □ 10.65 (br. s., 1H), 7.40 (br. s., 1H), 6.93 (br. s., 2H), 4.06 (br. s., 4H), 1.02 (br. s., 4H), 0.20 (s, 6H); $^{13}$C NMR (100 MHz, CDCl$_3$) δ 161.5, 160.5 (dd, J=241.9, 11.6 Hz), 156.5 (dd, J=250.5, 17.7 Hz), 137.2 (t, J=13.1 Hz), 130.0, 128.9, 127.7, 113.9 (d, J=21.6 Hz), 100.4, 95.7 (dd, J=30.0, 23.1 Hz), 94.1 (dd, J=26.2, 4.6 Hz), 46.4, 43.6, 15.0, 14.0, −3.0; HRMS (ESI): m/z calculated for C$_{15}$H$_{19}$ON$_2$F$_2$Si[M+H]$^+$ 309.1229 found 309.1237.

Example 12: N-(4,4-dimethylpiperidin-1-yl)-4,6-difluoro-1H-indole-2-carboxamide (l)

Compound (l)

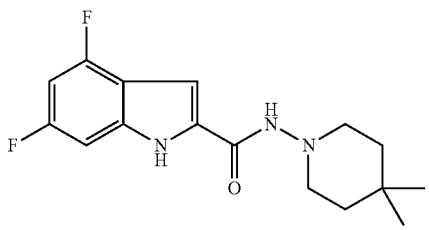

White solid product (16 mg, 40% yield); $^1$H NMR (400 MHz, CDCl$_3$) δ 10.22 (br. s., 1H), 7.66 (br. s., 1H), 6.97 (t, J=7.9 Hz, 1H), 6.90-6.81 (m, 1H), 6.64 (t, J=9.7 Hz, 1H), 3.11-3.08 (m, 1H), 2.93 (br. s., 2H), 2.67 (t, J=11.0 Hz, 1H), 1.73 (d, J=11.6 Hz, 2H), 1.62 (br. s., 2H), 1.07 (br. s., 2H), 1.01 (br. s., 4H).

Example 13: 4,6-dichloro-N-(4,4-dimethyl-1,4-azasilinan-1-yl)-1H-indole-2-carboxamide hydrochloride (m)

Compound (m)

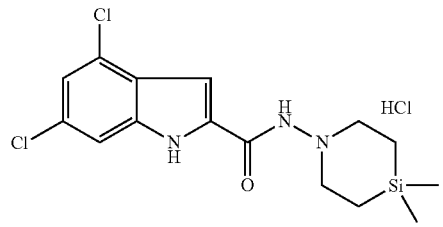

Compound (f) (10 mg) dissolved in dry dioxane (2 mL), 4M HCl in dioxane (2 mL) was added dropwise at 0° C. and reaction mixture was stirred for 2 h at 35° C. Solid obtained was then filtered and dried under vacuum to obtain pure white solid product.

Example 14: 4,6-dichloro-N-(4,4-dimethylpiperidin-1-yl)-1H-indole-2-carboxamide hydrochloride (n)

Compound (n)

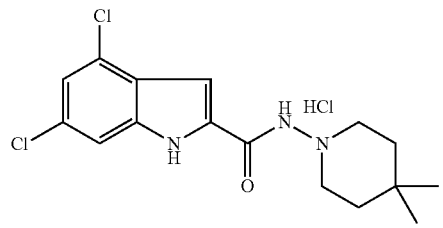

Compound h (10 mg) dissolved in dry dioxane (2 mL), 4M HCl in dioxane (2 mL) was added dropwise at 0° C. and reaction mixture was stirred for 2 h at 35° C. Solid obtained was then filtered and dried under vacuum to obtain pure white solid product.

Example 15: 1H-indole-2-carbohydrazide (o)

Compound (o)

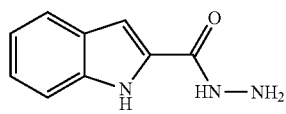

Indole carboxylic acid (1 eq) was dissolved in SOCl$_2$ and refluxed for 2 h at 100° C., the excess SOCl$_2$ was removed through vacuum and the crude compound was dissolved in EtOH followed by the addition of NH$_2$NH$_2$·H$_2$O was done.

The reaction mixture was refluxed for 2 h at 100° C., the reaction mixture was diluted with water (10 mL), extracted with Ethyl acetate (15 mL×3), saturated aq. NaHCO$_3$ solution (10 mL×2) and dried over anhydrous Na$_2$SO$_4$ concentrate in vacuum. The crude material obtained after removal of solvent was recrystallized from EtOH.

White solid product (38 mg, 42% yield); $^1$H NMR (400 MHz, DMSO-d$_6$) δ=$^1$H NMR (400 MHz, DMSO) δ 11.61 (s, 1H), 9.79 (s, 1H), 7.59 (d, J=7.9 Hz, 1H), 7.44 (d, J=8.1 Hz, 1H), 7.22-7.00 (m, 3H), 4.52 (s, 2H); $^{13}$C NMR (101 MHz, CHLOROFORM-d) δ=$^{13}$C NMR (101 MHz, CDCl$_3$) δ 161.7, 136.7, 130.9, 127.6, 123.6, 121.9, 120.2, 112.7, 102.3.

Example 16: N',N'-diethyl-1H-indole-2-carbohydrazide (p)

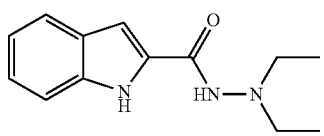

Compound (p)

General Procedure for Di-Alkylation:

1H-indole-2-carbohydrazide (1 eq), K$_2$CO$_3$ (4 eq) and NaI (2 eq) charged in R.B. and applied vacuum for 20 min. Then solvent (DMF=10 mL) was added. Slow addition of halide compound of Formula 3 was done in 30 minutes. The reaction mixture was kept at 100° C. for 12 h. The reaction mixture was diluted with ice cold water (10 mL), extracted with Ethyl acetate (15 mL×3), dried over anhydrous Na$_2$SO$_4$ concentrate in vacuum. The crude material obtained after removal of solvent was purified by column chromatography to obtain pure material.

White solid product (50 mg, 44% yield); 1H NMR (200 MHz, CDCl$_3$) δ 10.31 (d, J=49.1 Hz, 1H), 7.98-7.36 (m, 5H), 6.89 (s, 1H), 3.26 (dt, J=14.3, 7.1 Hz, 3H), 2.94 (dd, J=12.5, 6.9 Hz, 1H), 1.44 (dt, J=11.0, 7.1 Hz, 6H).

Example 17: N',N'-dibutyl-1H-indole-2-carbohydrazide (q)

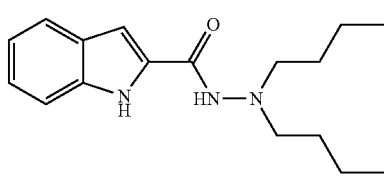

Compound (q)

White solid product (140 mg, 49% yield); 1H NMR (200 MHz, CDCl$_3$) δ 10.21 (s, 1H), 7.78-7.07 (m, 5H), 6.67 (s, 1H), 3.05-2.91 (m, 3H), 2.74-2.60 (m, 1H), 1.65-1.62 (m, 4H), 1.43-1.35 (m, 4H), 0.97-0.87 (m, 6H).

Example 18: N',N'-dipentyl-1H-indole-2-carbohydrazide (r)

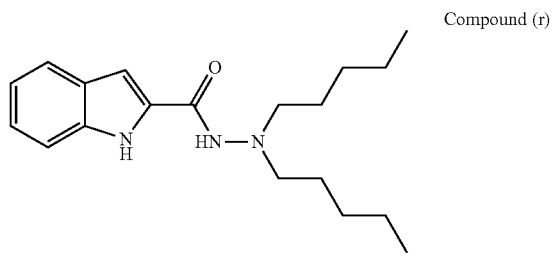 [SMILES: CCCCCN(CCCCC)NC(=O)c1cc2ccccc2[nH]1]

Compound (r)

White solid product (80 mg, 52% yield); $^1$H NMR (400 MHz, CDCl$_3$) δ 10.48 (s, 1H), 7.75 (d, J=8.0 Hz, 0.5H), 7.67 (d, J=7.6 Hz, 1H), 7.55-7.45 (m, 1H), 7.38-7.27 (m, 1H), 7.19 (ddd, J=14.1, 12.3, 5.5 Hz, 1H), 7.06 (s, 0.5H), 3.01 (s, 2H), 2.97-2.88 (m, 1H), 2.72-2.61 (m, 1H), 1.75-1.55 (m, 4H), 1.43-1.21 (m, 8H), 0.87 (tt, J=13.7, 6.9 Hz, 6H); $^{13}$C NMR (100 MHz, CHLOROFORM-d) δ=13C NMR (101 MHz, CDCl3) δ 163.7, 161.3, 136.8, 136.0, 129.5, 129.8, 127.5, 127.4, 124.8, 124.5, 122.5, 121.8, 120.6, 120.3, 112.3, 112.0, 110.4, 59.8, 58.5, 29.6, 29.4, 26.4, 22.6, 22.5, 14.0.

Example 19: N',N'-dihexyl-1H-indole-2-carbohydrazide (s)

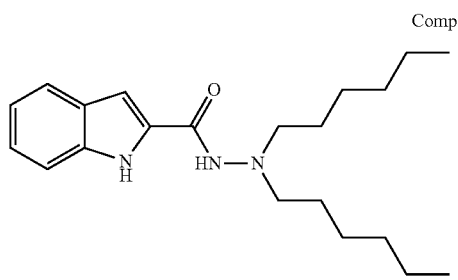

Compound (s)

White solid product (188 mg, 55% yield); 1H NMR (400 MHz, CDCl3) δ 10.49 (s, 1H), 7.78-7.65 (m, 2H), 7.55-7.46 (m, 1H), 7.37-7.25 (m, 2H), 7.17 (dt, J=7.1, 6.3 Hz, 1H), 7.06 (s, 1H), 2.94 (ddd, J=19.6, 15.7, 14.0 Hz, 3H), 2.72-2.59 (m, 1H), 1.71-1.51 (m, 4H), 1.43-1.14 (m, 13H), 0.86 (dt, J=10.2, 6.9 Hz, 6H); $^{13}$C NMR (100 MHz, CHLOROFORM-d) δ=13C NMR (101 MHz, CDCl$_3$) δ 163.7, 161.4, 136.8, 136.0, 129.1, 127.5, 127.4, 124.7, 124.4, 122.4, 121.8, 120.5, 120.3, 112.3, 112.0, 110.3, 59.8, 58.4, 31.7, 31.6, 27.1, 26.9, 26.6, 22.6, 14.0, 14.0.

Example 20: N-(piperidin-1-yl)-1H-indole-2-carboxamide (t)

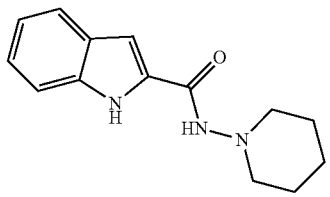

Compound (t)

White solid product (72 mg, 30% yield); 1H NMR (400 MHz, DMSO-D6) δ 11.50 (s, 1H), 9.34 (s, 1H), 7.54 (d, J=7.9 Hz, 1H), 7.38 (d, J=8.2 Hz, 1H), 7.12 (t, J=7.5 Hz, 1H), 7.06 (d, J=1.0 Hz, 1H), 6.98 (t, J=7.6 Hz, 1H), 3.02-2.62 (m, 4H), 1.73-1.50 (m, 5H), 1.33 (s, 2H); $^{13}$C NMR (100 MHz, DMSO-D6) δ=$^{13}$C NMR (101 MHz, DMSO-D6) δ 159.4, 136.8, 131.3, 127.5, 123.6, 121.9, 120.2, 112.7, 102.8, 55.9, 25.94, 23.64.

Example 21: N',N'-diallyl-1H-indole-2-carbohydrazide (u)

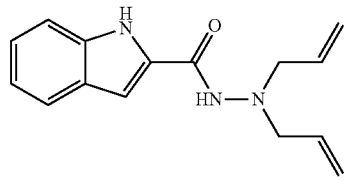

Compound (u)

White solid product (122 mg, 48% yield); 1H NMR (400 MHz, CDCl$_3$) δ 9.87 (d, J=24.9 Hz, 1H), 7.67 (dd, J=31.4, 8.2 Hz, 1H), 7.45 (d, J=8.2 Hz, 1H), 7.30 (q, J=7.7 Hz, 1H), 7.14 (t, J=7.5 Hz, 1H), 6.93 (s, 1H), 6.08-5.87 (m, 2H), 5.28 (dt, J=23.5, 15.6 Hz, 4H), 3.72 (s, 2H), 3.66-3.55 (m, 1H), 3.39 (dd, J=13.1, 7.0 Hz, 1H); 13C NMR (101 MHz, CDCl3) δ 163.5, 160.8, 136.7, 136.0, 131.9, 128.9, 127.4, 125.0, 124.9, 122.6, 122.0, 120.9, 120.5, 112.2, 112.0, 110.1, 61.3, 60.4.

Example 22: 4,6-dichloro-1H-indole-2-carbohydrazide (v)

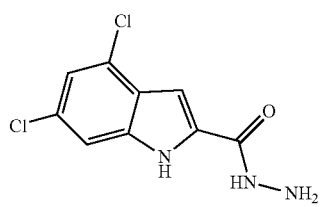

Compound (v)

White solid product (38 mg, 42% yield); $^1$H NMR (400 MHz, DMSO-d$_6$) δ 12.12 (s, 1H), 9.99 (s, 1H), 7.43 (s, 1H), 7.21 (s, 2H), 4.57 (s, 2H); $^{13}$C NMR (10 MHz, CHLOROFORM-d) δ=13C NMR (101 MHz, CDCl3) δ 160.6, 137.1, 132.7, 127.9, 126.6, 125.3, 119.8, 111.5, 100.4.

Example 23: 4,6-dichloro-N',N'-diethyl-1H-indole-2-carbohydrazide (w)

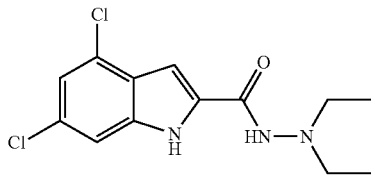

Compound (w)

LCMS (ESI): m/z calculated for $C_{13}H_{15}Cl_2N_3O$ [M+H]$^+$ 299.0592 found 300.05.

Example 24: N',N'-dibutyl-4,6-dichloro-1H-indole-2-carbohydrazide (x)

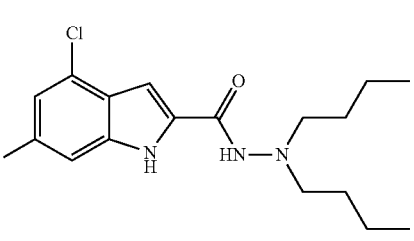

Compound (x)

White solid product (45 mg, 25% yield); 1H NMR (400 MHz, CDCl$_3$) δ 10.83 (d, J=103.1 Hz, 1H), 7.68 (s, 1H), 7.46-7.38 (m, 1H), 7.17-7.11 (m, 1H), 7.01 (d, J=41.2 Hz, 2H), 2.91 (t, J=7.6 Hz, 3H), 2.71-2.59 (m, 1H), 1.66-1.49 (m, 4H), 1.46-1.25 (m, 4H), 0.87 (dt, J=17.2, 7.3 Hz, 6H); $^{13}$C NMR (10 MHz, CHLOROFORM-d) δ 163.1, 160.7, 137.2, 136.4, 130.7, 130.4, 130.1, 130.0, 128.3, 127.4, 125.3, 125.3, 121.0, 120.8, 111.1, 110.8, 108.7, 100.5, 59.6, 58.3, 29.4, 28.8, 20.6, 20.4, 14.0, 14.0.

Example 25: 4,6-dichloro-N',N'-dipentyl-1H-indole-2-carbohydrazide (y)

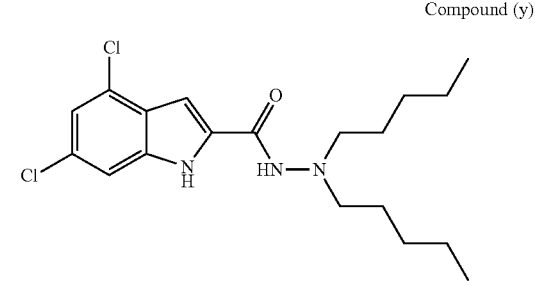 [SMILES: CCCCCN(CCCCC)NC(=O)c1cc2c(Cl)cc(Cl)cc2[nH]1]

Compound (y)

LCMS (ESI): m/z calculated for $C_{19}H_{77}Cl_2N_3O$ [M+H] 383.1531 found 384.1.

Example 26: 4,6-dichloro-N',N'-dihexyl-1H-indole-2-carbohydrazide (z)

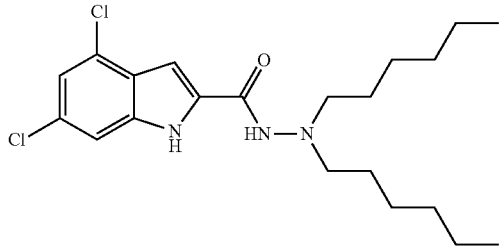

Compound (z)

White solid product (110 mg, 27% yield); 1H NMR (400 MHz, CDCl$_3$) δ 11.05 (d, J=135.9 Hz, 1H), 7.71 (dd, J=2.1, 0.9 Hz, 1H), 7.42 (d, J=1.0 Hz, 1H), 7.29 (d, J=3.6 Hz, 1H), 7.12 (dd, J=7.1, 1.6 Hz, 1H), 6.99 (d, J=1.3 Hz, 1H), 3.03-2.84 (m, 3H), 2.72-2.57 (m, 4H), 1.66-1.47 (m, 4H), 1.40-1.15 (m, 8H), 0.88-0.75 (m, 6H); $^{13}$C NMR (100 MHz, CDCl$_3$) δ 163.4, 160.8, 137.3, 136.5, 130.7, 130.3, 130.0, 129.9, 128.3, 127.7, 125.3, 125.3, 120.9, 120.7, 111.2, 110.8, 108.7, 100.7, 59.7, 58.3, 29.6, 29.4, 27.0, 26.4, 22.6, 22.5, 14.1, 14.0.

Example 27: 4,6-dichloro-N-(piperidin-1-yl)-1H-indole-2-carboxamide (aa)

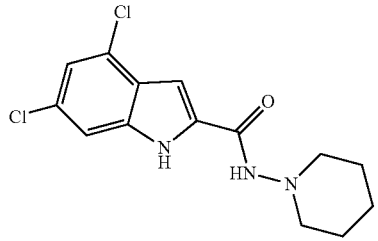

Compound (aa)

White solid product (65 mg, 21% yield); δ1H NMR (400 MHz, DMSO-D6) δ 12.04 (s, 1H), 9.55 (s, 1H), 7.37 (d, J=0.8 Hz, 1H), 7.20 (d, J=1.8 Hz, 1H), 7.17 (d, J=1.8 Hz, 1H), 2.87-2.69 (m, 4H), 1.64-1.49 (m, 4H), 1.33 (d, J=3.4 Hz, 2H); $^{13}$C NMR (100 MHz, DMSO-D6) δ=13C NMR (101 MHz, DMSO-D6) δ 158.3, 137.2, 133.1, 128.1, 126.7, 125.2, 119.9, 111.5, 100.9, 56.0, 25.8, 23.5.

Example 28: N',N'-diallyl-4,6-dichloro-1H-indole-2-carbohydrazide (bb)

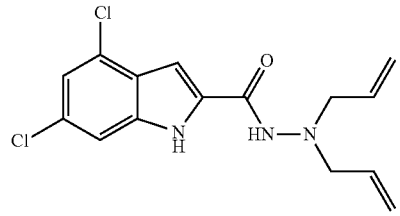

Compound (bb)

White solid product (58 mg, 18% yield); 1H NMR (400 MHz, DMSO-D6) δ 12.09 (d, J=1.6 Hz, 1H), 9.45 (s, 1H), 7.48 (s, 1H), 7.42-7.39 (m, 1H), 7.22-7.18 (m, 2H), 5.86 (ddd, J=12.6, 10.3, 5.2 Hz, 2H), 5.21 (dd, J=17.3, 1.7 Hz, 2H), 5.08 (dd, J=10.2, 1.7 Hz, 2H), 3.49 (d, J=6.3 Hz, 3H); 13C NMR (100 MHz, DMSO-D6) δ 159.5, 137.1, 135.1, 132.8, 128.0, 126.6, 125.1, 119.8, 118.2, 111.4, 100.7, 59.6.

Advantages of the Invention

Novel indole carboxamide compound(s) of Formula (I) is disclosed.

Simple and cost-effective process for the preparation of compound(s) of formula (I) is disclosed.

The compounds of Formula (I) show anti-mycobacterial activity. The compounds of Formula (I) show improvement in pharmacokinetics, in particular solubility.

The compounds of Formula (I) may show antimalarial activity or antifungal activity.

We claim:

1. An indole compound of Formula (I) or a pharmaceutically acceptable salt

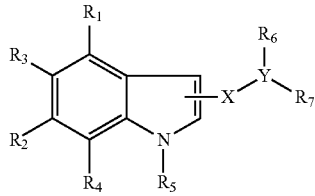

Formula (I)

wherein:

X is selected from the group consisting of —CO, and —CONH;

Y is selected from the group consisting of —NH, and —N—;

$R_1$, $R_2$, $R_3$, $R_4$, $R_5$ are same or different and each is independently selected from the group consisting of hydrogen, alkyl (linear or branched), cycloalkyl, aryl, heterocyclyl, heteroaryl, alkyl cycloalkyl, alkylaryl, alkylheterocyclyl, alkyl heteroaryl, alkenyl, halogen, trifluromethyl, nitro, amide, ester, cyano, alkoxy, alkylamino, and arylamino;

$R_6$ and $R_7$ together form a cyclic ring and comprises at least one —Si— atom.

2. The indole compound of Formula (I) as claimed in claim 1 is selected from the group consisting of:
   i. (4,4-dimethyl-1,4-azasilinan-1-yl)-1H-indole-2-carboxamide (c);
   ii. (4,4-dimethyl-1,4-azasilinan-1-yl)(1H-indol-2-yl)methanone (d);
   iii. 4,6-dichloro-N-(4,4-dimethyl-1,4-azasilinan-1-yl)-1H-indole-2-carboxamide (f);
   iv. (4,6-dichloro-1H-indol-2-yl)(4,4-dimethyl-1,4-azasilinan-1-yl)methanone (g);
   v. N-(4,4-dimethyl-1,4-azasilinan-1-yl)-4,6-difluoro-1H-indol-2-carboxamide (j);
   vi. (4,6-difluoro-1H-indol-2-yl)(4,4-dimethyl-1,4-azasilinan-1-yl)methanone (k);
   vii. 4,6-dichloro-N-(4,4-dimethyl-1,4-azasilinan-1-yl)-1H-indole-2-carboxamide hydrochloride (m).

3. A process for preparation of a compound of Formula (I) for preparing compounds a, b, c, d, e, f, and g as claimed in claim 2, wherein said process comprises adding a coupling agent to a solution of an indole compound of Formula 1 and an amine compound of Formula 2 prepared in dimethyl formamide (DMF) followed by stirring reaction mixture for a time period ranging from 10 to 18 hours at a temperature ranging from 25 to 35° C., to obtain the compound of Formula (I) for preparing the compounds c, d, f, g, j, k and m,

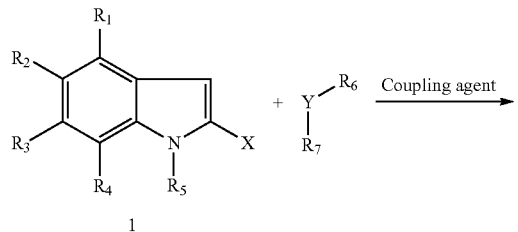

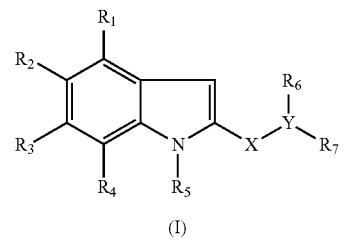

wherein:
X is selected from the group consisting of —CO, and —CONH;
Y is selected from the group consisting of —NH, and —N—;
$R_1$, $R_2$, $R_3$, $R_4$, $R_5$ are same or different and each is independently selected from the group consisting of hydrogen, alkyl (linear or branched), cycloalkyl, aryl, heterocyclyl, heteroaryl, alkyl cycloalkyl, alkylaryl, alkylheterocyclyl, alkyl heteroaryl, alkenyl, halogen, trifluromethyl, nitro, amide, ester, cyano, alkoxy, alkylamino, and arylamino;
$R_6$ and $R_7$ together form a cyclic ring and comprises at least one —Si— atom.

4. The process as claimed in claim 3, wherein said indole compound of Formula 1 is selected from the group consisting of 1H-indole-2carboxylic acid, 4,6-dichloro-1H-indole-2carboxylic acid, and 4,6-difluoro-1H-indole-2carboxylic acid.

5. The process as claimed in claim 3, wherein said amine compound of Formula 2 is selected from the group consisting of 4,4-dimethyl-1,4-azasilinan-1-amine, and 4,4-dimethyl-1,4-azasilinane.

6. The process as claimed in claim 3, wherein said coupling agent is selected from the group consisting of N-(3-Dimethylaminopropyl)-N'-ethylcarbodiimide hydrochloride (EDCCl), 1-hydroxybenzotriazole (HOBt), N,N-diisopropylethylamine (DIPAE) or (1-[Bis(dimethylamino)methylene]-1H-1,2,3-triazolo[4,5-b]pyridinium 3-oxid hexafluorophosphate [Hexafluorophosphate Azabenzotriazole Tetramethyl Uronium (HATU)] or mixture thereof.

7. A pharmaceutical composition of an indole compound of Formula (I) or a pharmaceutically acceptable salt, wherein said pharmaceutical composition comprises a therapeutically effective amount of the indole compound of Formula (I) or the pharmaceutically acceptable salt

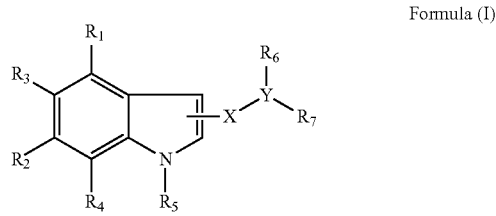

wherein:
X is selected from the group consisting of —CO, and —CONH;
Y is selected from the group consisting of —NH, and —N—;
$R_1$, $R_2$, $R_3$, $R_4$, $R_5$ are same or different and each is independently selected from the group consisting of hydrogen, alkyl (linear or branched), cycloalkyl, aryl, heterocyclyl, heteroaryl, alkyl cycloalkyl, alkylaryl, alkylheterocyclyl, alkyl heteroaryl, alkenyl, halogen, trifluromethyl, nitro, amide, ester, cyano, alkoxy, alkylamino, and arylamino;
$R_6$ and $R_7$ together form a cyclic ring and comprises at least one —Si— atom;
and a pharmaceutically acceptable carrier, a diluent or an excipient for treating a mycobacterial infection or an antimalarial infection or an antifungal infection in a subject in need thereof.

* * * * *